United States Patent
Matsuyama et al.

(10) Patent No.: US 7,223,857 B2
(45) Date of Patent: May 29, 2007

(54) CHAIN-SHORTENED POLYNUCLEOTIDE AND METHOD FOR PREPARATION THEREOF

(75) Inventors: Shinji Matsuyama, Kyoto (JP); Kouichi Ishiyama, Ibaraki (JP); Junzo Seki, Osaka (JP); Tadaaki Ohgi, Ibaraki (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 256 days.

(21) Appl. No.: 10/873,797

(22) Filed: Jun. 22, 2004

(65) Prior Publication Data

US 2004/0235044 A1    Nov. 25, 2004

Related U.S. Application Data

(62) Division of application No. 09/913,521, filed on Aug. 13, 2001, now Pat. No. 6,780,429.

(51) Int. Cl.
*C07H 21/00*    (2006.01)
*C07H 21/04*    (2006.01)
*C12Q 1/68*    (2006.01)

(52) U.S. Cl. .......................... 536/25.3; 536/23.1; 435/6

(58) Field of Classification Search .................... None
See application file for complete search history.

(56) References Cited

OTHER PUBLICATIONS

Wallace et al. Biochemistry 1981, vol. 20, pp. 5364-5368.*

* cited by examiner

*Primary Examiner*—James Schultz
*Assistant Examiner*—Tracy Vivlemore
(74) *Attorney, Agent, or Firm*—Greenberg Traurig, LLP; Gerard F. Diebner

(57) ABSTRACT

The present invention provides a chain-shortened polynucleotide wherein the proportion of a 2'-5' phosphodiester bond is up to 3% based on the whole phosphodiester bonds or a salt thereof and a pharmaceutical composition containing the same, and a method for producing the same.

3 Claims, No Drawings

CHAIN-SHORTENED POLYNUCLEOTIDE AND METHOD FOR PREPARATION THEREOF

CROSS-REFERENCE TO RELATED APPLICATION

This application is a divisional application of U.S. Ser. No. 09/913,521, filed on Aug. 13, 2001 now U.S Pat. No. 6,780,429. The disclosure of that application is expressly incorporated herein by reference.

TECHNICAL FIELD

The present invention relates to a chain-shortened polynucleotide particularly useful as a medicine, and a method for preparing the same. More specifically, the present invention relates to a synthetic chain-shortened polynucleotide or salts thereof, wherein the proportion of a 2'-5' phosphodiester bond is up to 3% based on the whole phosphodiester bonds, i.e., the rate of phosphate groups rearranged from 3' position to 2' position based on the whole phosphate groups of phosphodiester bonds (the phosphate rearrangement rate) is up to 3%, and a method for preparing the same.

TECHNICAL BACKGROUND

Polynucleotides typified by polyinosinic—polycytidylic acid, i.e., poly(I)-poly(C), are well-known compounds in the art, and the potentiality as a medicine for treating hepatitis or cancer have been investigated in view of their interferon inducing action, immune activating action, and the like.

The pharmacological action of these polynucleotides has high correlation with the chain length, and longer the chain length, stronger the interferon inducing action and the like. On the other hang, longer the chain length, stronger the toxicity manifested.

Recently, there has been an approach for reducing toxicity with maintaining useful pharmacological action of a polynucleotide, by a method wherein a synthetic polynucleotide having a relatively shorter chain prepared by the hydrolysis of a polynucleotide is enclosed in a carrier such as cationic liposome effective for introducing a medicament into a cell (e.g., PCT WO99/20283, PCT WO99/48531).

It is known that when a polynucleotide is hydrolyzed to shorten the chain length as described above, some phosphate groups cause intramolecular rearrangement from 3' position to 2' position through a mechanism called pseudo rotation simultaneously with the chain-shortening (see, e.g., "Protein Nucleic acid Enzyme", Vol. 40, No. 10, pp. 1323 to 1332 (1995)). As a result, a portion of 3'-5' phosphodiester bonds in the chain-shortened polynucleotide molecule are replaced by 2'-5' phosphodiester bonds. It has never been known whether or not such a phosphate rearrangement phenomenon would affect the pharmacological action.

DESCRIPTION OF INVENTION

An object of the present invention is to provide, firstly, a chain-shortened polynucleotide or salt thereof and a double stranded chain-shortened polynucleotide or salt thereof, which are safe and effective as a medicine.

The present inventors have been intensively studied and found that the problems described above can be solved by a chain-shortened polynucleotide which contains 2'-5' phosphodiester bond produced mainly in a chain-shortening reaction only at a particular proportion or less, or a salt thereof, and accomplished the present invention.

An aspect of the present invention is a chain-shortened polynucleotide containing a 2'-5' phosphodiester bond at a proportion of 3% or less, preferably 2% or less, based on the whole phosphodiester bonds, or salt thereof.

The present invention includes also as an embodiment a double stranded chain-shortened polynucleotide or salt thereof, which is formed from two chain-shortened polynucleotides or salts thereof capable of forming a double strand, which is inclusive in the above-described chain-shortened polynucleotides containing a 2'-5' phosphodiester bond at a proportion of 3% or less, preferably 2% or less, based on the whole phosphodiester bonds. Further, the present invention also includes a composition comprising a complex formed-from a carrier effective for introducing a medicament into a cell and the above-described chain-shortened polynucleotide or salt thereof wherein the proportion of a 2'-5' phosphodiester bond is 3% or less based on the whole phosphodiester bonds, or the double stranded chain-shortened polynucleotide or salt thereof formed from two chain-shortened polynucleotides or salts thereof capable of forming a double strand as an essential ingredient.

The polynucleotide used in the present invention is a compound comprising at least about 20 nucleotides, which is formed by polymerizing linearly through a phosphodiester bond and includes synthetic and natural compounds. Specific examples include polyinosinic acid [namely, poly(I)] or an analogue thereof, polycytidylic acid [namely, poly(C)] or an analogue thereof, polyadenylic acid [namely, poly(A)] or an analogue thereof, and polyuridylic acid [namely, poly(U)] or an analogue thereof.

The polyinosinic acid analogue is a homopolymer in which all or a part of inosinic acid is chemically modified or a copolymer of inosinic acid with other nucleotide, for example, poly(7-deazainosinic acid) and poly(2'-azidoinosinic acid). The polycytidylic acid analogue is a homopolymer in which all or a part of cytidylic acid is chemically modified or a copolymer of cytidylic acid with other nucleotide, for example, poly(5-bromocytidylic acid), poly(2-thiocytidylic acid), poly(cytidine-5'-thiophosphoric acid), poly(cytidylic acid, uridylic acid), poly(cytidylic acid, 4-thiouridylic acid) and poly(1-vinylcytidylic acid). The polyadenylic acid analogue and polyuridylic acid analogue are defined likewise. Among them, polyinosinic acid and polycytidylic acid are suitable in the present invention.

The average chain length of the chain-shortened polynucleotide of the present invention is suitably from 0.1 k bases to 1 k base. The term "base" means the number of base and "1 k base" indicates a base number of 1000, and hereinafter, "base(s)" is abbreviated to "b". The mean chain length is preferably from 200 b to 800 b, and more preferably from 300 b to 600 b. The average chain length can be determined easily, for example, by gel permeation chromatography (hereinafter, referred to as "GPC") as described hereinafter in Experiment 5.

In the chain-shortened polynucleotide of the present invention, the phosphate rearrangement rate is 3% or less, preferably 2% or less or between 0.1% and 2%, and more preferably 1% or less or between 0.1% and 1%.

The rearrangement of phosphate group from 3' position to 2' position in polynucleotide can be confirmed easily, for example, by a method as described in Experiment 6.

Namely, a polynucleotide is degraded with nuclease $P_1$, which specifically hydrolyzes a 3'-5' phosphodiester bond to such levels as a nucleoside, nucleotide and oligonucleotide, and then treated with an alkaline phosphatase, which specifically hydrolyzes a terminal phosphate group, to convert the whole nucleotides into nucleosides. On the other hand, an oligonucleotide having a 2'-5' phosphodiester bond, which is not hydrolyzed by the nuclease $P_1$ is not degraded till nucleoside even by the treatment with an alkaline phosphatase because an intramolecular 2'-5' phosphodiester bond is not hydrolyzed. The phosphate rearrangement rate can be calculated by determining nucleosides and oligonucleotides (most of them are dimers) by liquid chromatography, or the like.

Examples of a pair of chain-shortened polynucleotides capable of forming a double strand in connection with the present invention include polyinosinic acid and polycytidylic acid, polyadenylic acid and polyuridylic acid, polyinosinic acid analogue and polycytidylic acid, polyinosinic acid and polycytidylic acid analogue, polyinosinic acid analogue and polycytidylic acid analogue, polyadenylic acid analogue and polyuridylic acid, polyadenylic acid and polyuridylic acid analogue, and polyadenylic acid analogue and polyuridylic acid analogue. Therefore, examples of the double stranded chain-shortened polynucleotide formed between two chain-shortened polynucleotides capable of forming a double strand include polyinosinic-polycytidylic acid, polyadenylic-polyuridylic acid, polyinosinic analogue-polycytidylic acid, polyinosinic-polycytidylic acid analogue, polyinosinic analogue-polycytidylic acid analogue, polyadenylic analogue-polyuridylic acid, polyadenylic-polyuridylic acid analogue, and polyadenylic analogue-polyuridylic acid analogue. For the purposes of the present invention, polyinosinic-polycytidylic acid would be a preferred double stranded chain-shortened polynucleotide.

The average chain length of the above-described double stranded chain-shortened polynucleotide is reasonably regarded as corresponding to the average chain length of the whole chain-shortened polynucleotides. Accordingly, the latter can be used to show the apparent average chain length of the double stranded chain-shortened polynucleotide in terms of the number of base pairs (bp). Therefore, the average chain length of the above-described double stranded chain-shortened polynucleotide is from 0.1 k bp to 1 k bp. The term "bp" means the number of base pairs and "1 k bp" corresponds to a base pair number of 1000. The average chain length of the double-stranded polynucleotide is preferably from 200 bp to 800 bp, and more preferably from 300 bp to 600 bp.

The salt of a chain-shortened polynucleotide and that of a double stranded chain-shortened polynucleotide of the present invention are not particularly restricted as far as they are pharmaceutically acceptable, and examples thereof include a sodium salt and potassium salt.

As a carrier effective for introducing a medicament into a cell, those having a positive charge are exemplified, and specific examples include cationic polymers such as poly-L-lysine, cationic liposomes such as Lipofectin®, Lipofectamine®, Lipofectace®, DMRIE-C®, etc., and carriers considered to be of the same kind which are disclosed in PCT WO94/19314. The carriers for carrying a medicament are formed, for example, from 2-O-(2-diethylaminoethyl) carbamoyl-1,3-O-dioleoyl glycerol of the formula [I]:

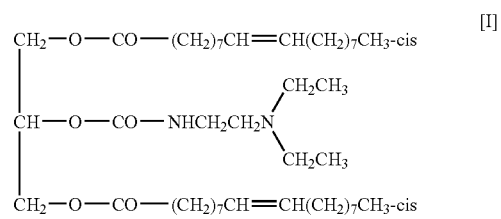

and a phospholipid (e.g., phosphatidyl choline, phosphatidyl ethanolamine, yolk lecithin, soy bean lecithin, hydrogenated phospholipid thereof) as essential structural components.

It is believed that the above-described cationic liposome is positively charged and forms an electrostatic complex with a negatively charged polynucleotide or oligonucleotide. When the resultant complex fuses with cell membrane, the polynucleotide or oligonucleotide is concurrently introduced into the cell. Such a complex is sometimes called "lipoplex".

A method for preparing the chain-shortened polynucleotide of the present invention will be described in detail. The chain-shortened polynucleotide of the present invention can be prepared, for example, by hydrolyzing the starting polynucleotide in solution at suitable pH range while heating at a suitable temperature range. The suitable pH of the aqueous solution in this procedure is basic, i.e., pH 7 or more, preferably pH 7 to 10. Considering the reaction rate of the chain-shortening reaction and the stability of base moiety, more preferable pH of the solution would be between 8 and 9. The reaction temperature is suitably within a range of 20 to 110° C., preferably 40 to 100° C., from the standpoint of the stability of a base. However, considering the sufficient hydrolysis rate and the stability of base moiety, more preferable reaction temperature would be between 50 and 90° C.

More specifically, for example, a polynucleotide is dissolved in water such as injectable water, distilled water for injection or physiological saline with stirring, and pH of the solution is adjusted to 8 to 9 with a buffer or a pH regulator. When the hydrolysis is conducted by heating the solution at reaction temperature ranging from 50 to 90° C. for 0.5 to 60 hours while monitoring the average chain length and the phosphate rearrangement rate, a chain-shortened polynucleotide containing less phosphate groups rearranged and having an average chain length between 0.1 kb and 1 kb can be produced.

Pharmaceutically acceptable additives such as a buffer or a pH regulator may be used for adjusting pH. Specific examples include buffers and pH regulators such as aminoacetic acid (synonym: glycine), tris(hydroxymethyl)aminomethane (synonym: Tris), sodium carbonate, sodium hydrogen carbonate (synonym: sodium bicarbonate), sodium hydroxide, diethanolamine, triethanolamine and the like. There are no limitations regarding the kind, combination, concentration and the like of these additives.

Monomers and unnecessary salts, impurities, by-products produced during the chain-shortening reaction and the like can be removed from the system by treating the reaction solution by dialysis or with activated carbon.

The chain-shortened polynucleotide of the present invention can also be prepared by treating the starting polynucleotide in solution with a phosphodiesterase at suitable pH range while heating at a suitable temperature range. The suitable pH of the aqueous solution in this procedure is between 4 and 9, preferably, between 5 and 8. Considering the phosphate rearrangement during the chain-shortening reaction, more preferable pH of the solution would be between 6 and 7. The reaction temperature is suitably within a range of 20 to 60° C., preferably 25 to 50° C., from the standpoint of the characteristics of the enzyme. However, more preferable reaction temperature would be between 30 and 40° C. taking the sufficient hydrolysis rate, the avoidance of influence of non-enzymatic hydrolysis such as hydrolysis with heat, and the prevention of phosphate-group rearrangement into consideration.

More specifically, for example, a polynucleotide is dissolved in water such as injectable water, distilled water for injection or physiological saline with stirring. The pH of the solution is optionally adjusted by adding a buffer or a pH regulator, if necessary. To the solution is added phosphodiesterase such as nuclease $P_1$ and the resultant mixture is subjected to the chain-shortening reaction at temperature from 30 to 40° C. while monitoring the average chain length and phosphate rearrangement rate to obtain a chain-shortened polynucleotide containing less phosphate groups rearranged and having an average chain length between 0.1 kb and 1 kb. There are no limitations regarding the enzyme concentration or reaction conditions.

Monomers and unnecessary salts, impurities, by-products produced during the chain-shortening reaction and the like can be removed from the system by treating the reaction solution by the ethanol precipitation method, dialysis or with activated carbon.

The chain-shortened polynucleotide can be purified by an appropriate separation method with a membrane. For example, membrane ultrafiltration is suited for the purpose of fractionating polynucleotides of average chain length between 0.1 kb and 1 kb of the present invention. There are no limitations regarding the quality of material or the pore size of the membrane.

As a starting material, any polynucleotides can be used regardless of origin such as natural or synthetic, the kind of salt or the chain length. Examples of natural polynucleotide include tRNA and polyadenylic acid. On the other hand, a synthetic polynucleotide can be produced from an RNA synthetase such as polynucleotide phosphorylase or immobilized enzymes thereof. Further, sodium polyinosinate, sodium polycytidylate, etc., which are commercially available as interferon inducing reagents, are also usable as a starting material.

The double stranded chain-shortened polynucleotide of the present invention can be prepared by mixing, in a suitable solution (for example, 0.15 M NaCl-containing 10 mM Tris-hydrochloric acid buffer (Tris-HCl buffer, pH7)), two chain-shortened polynucleotides capable of forming a double strand among chain-shortened polynucleotides containing less phosphate groups rearranged as prepared in the above, or alternatively, by allowing them to anneal in a conventional manner. As the annealing method, there is, for example, a method in which a solution containing two chain-shortened polynucleotides capable of forming a double strand is heated up to 70 to 80° C., and then cooled gradually.

A chain-shortened polynucleotide with less phosphate groups rearranged or a double stranded chain-shortened polynucleotide with less phosphate groups rearranged obtained as described above can be treated by lyophilization to give a lyophilized product storable for a long period. The lyophilization treatment can be conducted in a conventional manner. For example, a lyophilized product can be obtained as follows: a solution of a chain-shortened polynucleotide obtained under the conditions above is sterilized by filtration, the filtrate is then poured on a metal bat previously treated by dry heat sterilization, a pre-freezing is conducted at a shelf temperature from −40 to −20° C. for about 1 to 4 hours, and primary drying is conducted before the secondary drying which is effected under reduced pressure at a shelf temperature from 15 to 30° C. (for about 10 to 50 hours). Generally, such a lyophilized product can be used after reconstitution (re-dissolution) by the addition of an appropriate solution such as injectable water, distilled water for injection, physiological saline, maltose solution, glucose solution, or the like.

The composition of the present invention can be prepared in a manner similar to those generally used for the preparation of liposome, which composition comprises a complex (hereinafter, referred to as the present complex) formed with a carrier effective for introducing a medicament into a cell and a two chain-shortened polynucleotide containing 2'-5' phosphodiester bonds at proportion of 3% or less based on the whole phosphodiester bonds and being capable of forming a double strand, or a double-stranded chain-shortened polynucleotide formed between the said two chain-shortened polynucleotides capable of forming a double strand as an essential ingredient. Specifically, a composition for injection of the present invention can be prepared by the following steps comprising adding water (injectable water, distilled water for injection, physiological saline and the like) to a carrier effective for introducing a medicament into a cell, for example, a cationic liposome or raw material thereof (e.g., glycerol derivative such as 2-O-(2-diethylaminoethyl)carbamoyl-1,3-O-dioleoyl glycerol and the like and phospholipid); stirring the mixture; treating the mixture with a suitable device for dispersion, for example, a homomixer, a homogenizer, a ultrasonic dispersing device, a ultrasonic homogenizer, a high pressure emulsifying dispersing device, Microfluidizer (trade name), Nanomizer (trade name), De Bee 2000 (trade name), Ultimizer (trade name) or Manton-Gaulin type high pressure homogenizer; adding a chain-shortened polynucleotide or a double stranded chain-shortened polynucleotide of the present invention to the resultant lipid dispersion; re-dispersing the mixture by treating with a suitable dispersing device; and then subjecting the resultant composition to sterilization by filtration or the like. Any other additives can be added at an appropriate step during the preparation without any particular limitation. Alternatively, a composition of the present invention containing the present complex can be prepared as follows. Thus, a mixture of a carrier effective for introducing a medicament into a cell, for example, a cationic liposome or raw material thereof (e.g., glycerol derivative such as 2-O-(2-diethylaminoethyl)carbamoyl-1,3-O-dioleoyl glycerol and the like and phospholipid) and a chain-shortened polynucleotide or a double stranded chain-shortened polynucleotide of the present invention is first prepared. To the previously prepared mixture is added water while conducting the dispersion treatment at the same time. Further, a composition of the present invention can also be prepared via a suitable crude dispersing step during the above-described methods.

The resultant composition of the present invention can be lyophilized, whereby a lyophilized preparation of a composition of the present invention storable for a long period is obtained. The lyophilization can be conducted in a conventional manner. For example, a given amount of a composition of the present invention, which has been obtained by the above-mentioned dispersion and sterilization by filtration, is dispensed into a vial. The lyophilization is carried out by subjecting the vial to pre-freezing at a temperature between about −40 and −20° C. for about 2 to 3 hours, the primary drying at a temperature between about 0 and 10° C. under reduced pressure, and the secondary drying at a temperature between about 15 and 25° C. under reduced pressure. Generally, after replacing the inner space with an inert gas such as nitrogen gas, the vial is capped to provide a lyophilized preparation of a composition of the present invention.

The lyophilized preparation of a composition of the present invention can be used after reconstitution by adding an appropriate solution before use. Examples of such a solution for reconstitution include injectable water, distilled water for injection, physiological saline, maltose solution, glucose solution and other general infusion solutions and the like.

The composition of the present invention and lyophilized preparation thereof can be used in the form of a pharmaceutical prepatration as a medicine. The composition of the present invention and lyophilized preparation as a medicine exhibits a pharmacological activity owing to the active polynucleotide. The specific examples of the medicine include interferon inducing agents, immune activating agents, intracellular nuclease activating agents, cancer treating or preventive agents, and hepatitis treating or preventive agents.

BEST MODE FOR CARRYING OUT THE PRESENT INVENTION

The following examples and experiments further illustrate the present invention in more detail. The present invention is not restricted by these examples and experiments at all.

REFERENCE EXAMPLE 1

To 8 g of trisodium inosine-5'-diphosphate and 1 g of magnesium chloride was added 500 mL of a 0.1 M glycine-sodium hydroxide buffer, and the mixture was stirred for dissolution. After the pH was adjusted to 9.3 by the addition of 6N sodium hydroxide, the mixture was allowed to stand for 1 hour at 38° C. To the mixture was added 1 mL of a polynucleotide phosphorylase solution, and the reaction was conducted at 38° C. for 18 hours. After the reaction was quenched by adding 25 mL of 0.2 M ethylenediaminetetraacetic acid (EDTA), 10 mL of saturated saline and 500 mL of absolute ethanol were added to precipitate polyinosinic acid (1973b).

REFERENCE EXAMPLE 2

To 10 g of trisodium cytidine-5'-diphosphate and 3 g of manganese chloride was added about 1 L of a 0.2 M sodium hydrogen carbonate-sodium hydroxide buffer, and the mixture was stirred for dissolution. After the pH was adjusted to 9.8 by the addition of 6N sodium hydroxide, the mixture was allowed to stand for about 1 hour at 36° C. To the mixture was added 2 mL of a purified polynucleotide phosphorylase solution, and the reaction was conducted at 36° C. for 24 hours. The reaction was quenched by adding 50 mL of 0.2 M EDTA. To the mixture were then added 20 mL of saturated saline and 1 L of absolute ethanol to precipitate polycytidylic acid (3300 b).

EXAMPLE 1

Polyinosinic acid obtained in Reference Example 1 was separated by centrifugation. The precipitate was re-dissolved in 500 mL of injectable water and subjected to dialysis. The inner solution after dialysis was treated with an activated carbon and filtrated to remove the activated carbon. To filtrate was added 6N sodium hydroxide to adjust to pH 8.5. The hydrolysis was conducted by heating at 70° C. for 8 hours to shorten the chain of polyinosinic acid. The resultant solution of chain-shortened polynucleotide was treated with an activated carbon, filtrated to remove the activated carbon, and dialyzed. The inner solution after dialysis was sterilized by filtration. The filtrate was subjected to lyophilization in a conventional manner to obtain 1.9 g of a lyophilized product of chain-shortened polynucleotide (polyinosinate, sodium salt) of the present invention with less phosphate groups rearranged (phosphate rearrangement rate: 0.2%, average chain length: 360 b).

EXAMPLE 2

Polycytidylic acid obtained in Reference Example 2 was separated by centrifugation. The precipitate was re-dissolved in 500 mL of injectable water and subjected to dialysis. The inner solution after dialysis was treated with an activated carbon and filtered to remove the activated carbon. To filtrate was added 6N sodium hydroxide to adjust pH to 9.0. The hydrolysis was conducted by heating at 80° C. for 4 hours to shorten the chain of polycytidylic acid. The resultant solution of chain-shortened polynucleotide was treated with an activated carbon, filtrated to remove the activated carbon, and dialyzed. The inner solution after dialysis was sterilized by filtration. The filtrate was lyophilized in a conventional manner to obtain 2.7 g of a lyophilized product of chain-shortened polynucleotide (polycytidylate, sodium salt) of the present invention with less phosphate groups rearranged (phosphate rearrangement rate: 0.1%, average chain length: 318 b).

EXAMPLE 3

To 1 g of sodium polyadenylate ($S°_{20,w}$ (sedimentation constant): 7.2, Seikagaku Corporation) was added 200 mL of 0.1 M Tris-HCl buffer (pH 8.0), and the mixture was stirred for dissolution Hydrolysis was conducted by heating at 60° C. for 48 hours to shorten the chain of polyadenylic acid while monitoring the average chain length according to the method described in Experiment 5. The solution of chain-shortened polynucleotide was subjected to dialysis. The inner solution after dialysis was subjected to lyophilization in a conventional manner to obtain 0.3 g of a lyophilized product of chain-shortened polynucleotide (polyadenylate, sodium salt) of the present invention with less phosphate groups rearranged (phosphate rearrangement rate: 1.9%, average chain length: 154 b).

EXAMPLE 4

To 1 g of sodium polyuridylate ($S°_{20,w}$ (sedimentation constant): 6.5, Seikagaku Corporation) was added 200 mL of 0.2 M glycine-NaOH buffer (pH 9.0), and the mixture was stirred for dissolution. Hydrolysis was conducted by heating at 60° C. for 25 hours to shorten the chain of the polyadenylic acid while monitoring the average chain length according to the method described in Experiment 5. The resultant solution of chain-shortened polynucleotide was subjected to dialysis. The inner solution of the dialysis was subjected to lyophilization in a conventional manner to obtain 0.2 g of a lyophilized product of chain-shortened polynucleotide (polyuridylate, sodium salt) of the present invention with less phosphate groups rearranged (phosphate rearrangement rate: 1.2%, average chain length: 108 b).

EXAMPLE 5

To 250 mg of sodium polyinosinate ($S^\circ_{20,w}$ (sedimentation constant): 8.8, Yamasa Corporation) was added 50 mL of 0.1 M Tris-HCl buffer (pH 8.0), and the mixture was stirred for dissolution. The solution was heated at a temperature from 50 to 120° C. suitable for chain-shortening. Polyinosinic acids having an arbitrary chain length were sampled while monitoring the average molecular length by the method described in Experiment 5. The results are shown in Table 1. The resultant sample solutions were dialyzed, and lyophilized in a conventional manner to obtain lyophilized products.

TABLE 1

| Temperature for chain-shortening reaction | Time for chain-shortening reaction | Average chain length | Phosphate rearrangement rate |
| --- | --- | --- | --- |
| 50° C. | 50 hours | 1419 b | 0.1% |
| 60° C. | 27 hours | 982 b | 0.1% |
| 70° C. | 12 hours | 524 b | 0.4% |
| 80° C. | 8 hours | 118 b | 1.2% |
| 90° C. | 3 hours | 84 b | 1.8% |
| 120° C. | 1 hour | 32 b | 6.8% |

EXAMPLE 6

To 250 mg of sodium polycytidylate ($S^\circ_{20,w}$ (sedimentation constant): 8.6, Yamasa Corporation) was added 50 mL of 0.1 M Tris-HCl buffer (pH 9.0), and the mixture was stirred for dissolution. The solution was heated at a temperature from 55 to 120° C. suitable for chain-shortening. Polycytidylic acids having an arbitrary chain length were sampled while monitoring the average molecular length by the method described in Experiment 5. The results are shown in Table 2. The resultant sample solutions were dialyzed, and lyophilized in a conventional manner to obtain lyophilized products.

TABLE 2

| Temperature for chain-shortening reaction | Time for chain-shortening reaction | Average chain length | Phosphate rearrangement rate |
| --- | --- | --- | --- |
| 55° C. | 52 hours | 1923 b | 0.1% |
| 65° C. | 48 hours | 907 b | 0.1% |
| 75° C. | 23 hours | 489 b | 0.3% |
| 80° C. | 12 hours | 139 b | 0.8% |
| 90° C. | 8 hours | 76 b | 1.2% |
| 120° C. | 1.5 hours | 27 b | 4.2% |

It is apparent from the results obtained in Examples 5 and 6 that, in the chain-shortening process of commercially available sodium polyinosinate or sodium polycytidylate, sufficient hydrolysis could not be achieved when the chain-shortening was carried out at 55° C. or below. As a result, the average chain length exceeded 1 kb even after about 50 hours of chain shortening reaction. On the other hand, in samples wherein the chain-shortening was carried out at 120° C. or 90° C., the control of the chain-shortening was difficult because of too fast hydrolysis rate. Particularly, in the sample wherein the chain shortening was carried out at 120° C., the chain was too much shortened to such an extent of around oligonucleotide level even after 1 to 1.5 hours of chain-shortening. In this sample, the phosphate rearrangement rate was high and degradation of base moiety was also recognized.

EXAMPLE 7

One hundred mg of sodium polyadenylate ($S^\circ_{20,w}$ (sedimentation constant): 7.2, Seikagaku Corporation) was dissolved in 100 mL of 0.1 M Tris-HCl buffer (pH 7.0). To the solution was added nuclease $P_1$ (derived from Penicillium citrinum, Seikagaku Corporation). The mixture was incubated at 25° C. for 3 hours while monitoring the average chain length according to the method described in Experiment 5 to shorten the chain of polyadenylic acid (phosphate rearrangement rate: 0.1%, average chain length: 287 b).

EXAMPLE 8

To 1 g of trisodium uridine-5'-diphosphate and 0.3 g of magnesium chloride was added 100 mL of a 0.2 M sodium hydrogencarbonate-sodium hydroxide buffer, and the mixture was stirred for dissolution. After adjusting pH to 9.5 with 1N sodium hydroxide, 0.2 mL of polynucleotide phosphorylase was added. The mixture was then allowed to react for 10 hours at 25° C. while monitoring the average chain length according to the method described in Experiment 5. After the reaction was quenched by adding 5 mL of 0.2 M EDTA, 2 mL of saturated saline and 100 mL of ethanol were added to precipitate polyuridylic acid (549b). The polyuridylic acid was separated by centrifugation. The precipitate was re-dissolved in 50 ml of injectable water and dialyzed. The inner solution of the dialysis was adjusted to pH 8.5 with 1N sodium hydroxide and hydrolyzed at 80° C. for 30 minutes to regulate the chain length of polyuridylic acid. The resultant solution of chain-shortened polynucleotide was subjected to membrane separation by ultrafiltration so as to adjust the chain-length distribution, as well as to remove the unnecessary salt, by-products during the chain-shortening reaction or the like (phosphate rearrangement rate: 0.1%, average chain length: 485 b).

EXAMPLE 9

To 1 g of 2-O-(2-diethylaminoethyl)carbamoyl-1,3-O-dioleoyl glycerol and 2 g of purified yolk lecithin was added 40 g of maltose dissolved in 100 mL of injectable water. The mixture was stirred and dispersed for 5 minutes with a homogenizer to obtain a crude dispersion of a cationic liposome (carrier). The crude dispersion was further dispersed for 1 hour with a laboratory small emulsifying dispersing device to obtain a cationic liposome solution. To the cationic liposome solution was added gradually about 50 mL of an aqueous solution containing 200 mg each of the chain-shortened sodium polyinosinate and sodium polycytidylate each containing less phosphate groups rearranged, which were obtained in Examples 1 and 2, with stirring. The mixture was then treated with a laboratory small emulsifying dispersing device for another 2 hours, and finally adjusted the volume to 400 mL with injectable water to obtain a composition containing the present complex. The composition containing the present complex was sterilized by filtration, dispensed in 1 ml aliquots into a vial, and converted into a lyophilized preparation in a conventional manner. When the lyophilized preparation was reconstituted by the addition of injectable water to make the volume 1 ml, the average particle diameter of the present complex was 133 nm when evaluated by the photon correlation method.

EXAMPLE 10

To 50 g of 2-O-(2-diethylaminoethyl)carbamoyl-1,3-O-dioleoyl glycerol and 25 g of soy bean lecithin was added 1 kg of sucrose dissolved in 3 L of injectable water. The mixture was stirred and dispersed for 30 minutes with a Manton-Gaulin type high pressure homogenizer, and the volume was adjusted to 5 L with injectable water to obtain a dispersion of a cationic liposome (carrier). To the carrier dispersion was added about 2 L of an aqueous solution containing 1 g each of the chain-shortened sodium polyinosinate and sodium polycytidylate each containing less phosphate groups rearranged, which were obtained in Examples 1 and 2, with stirring; The dispersion was adjusted to pH 5.5 with 1N hydrochloric acid and dispersed with a Manton-Gaulin type high pressure homogenizer for another 1 hour, and finally the volume was adjusted to 10 L with injectable water to obtain a composition containing the present complex. The composition containing the present complex was then dispensed in 20 mL aliquots into a vial and converted into a lyophilized preparation in a conventional manner. When the lyophilized preparation was reconstituted by the addition of injectable water to make the volume 20 ml, the average particle diameter of the present complex was 158 nm when evaluated by the photon correlation method.

EXAMPLE 11

To 1 g of 2-O-(2-diethylaminoethyl)carbamoyl-1,3-O-dioleoyl glycerol and 2 g of yolk phosphatide was added 40 g of glucose dissolved in 100 mL of injectable water. The mixture was stirred and dispersed for 5 minutes with a homogenizer, and the volume was adjusted to 500 mL to obtain a crude dispersion of a cationic liposome (carrier). The crude dispersion was further dispersed for 1 hour with a laboratory small emulsifying dispersing device to obtain a cationic liposome solution. The solution was dispensed in 10 mL aliquots into a vial and lyophilized in a conventional manner. To the lyophilized product was added 10 mL of an aqueous solution containing 5 mg each of the chain-shortened sodium polyinosinate, sodium polycytidylate each containing less phosphate groups rearranged, which were obtained in Examples 1, 2 or 5, 6, and 5 mg each of the commercially available sodium polyinosinate ($S°_{20,w}$ (sedimentation constant): 8.8, Yamasa Corporation) and sodium polycytidylate ($S°_{20,w}$ (sedimentation constant): 8.6, Yamasa Corporation). The mixture was subjected to the dispersion treatment for 10 minutes with a probe type ultrasonic dispersing device to obtain a composition containing the present complex.

EXAMPLE 12

An aqueous solution (1 mL) containing 100 μg each of the chain-shortened sodium polyadenylate and sodium polyuridylate each containing less phosphate groups rearranged, which were obtained in Examples 3 and 4, and 2 mL of an aqueous solution containing 2 mg of a commercially available Lipofectin (trade name) were mixed with stirring. The mixture was dispersed for 15 minutes with a probe type ultrasonic dispersing device to obtain a composition containing the present complex.

EXAMPLE 13

To about 200 mg of sodium polyinosinate ($S°_{20,w}$ (sedimentation constant): 8.8, Yamasa Corporation) was added 0.2 M acetic acid-sodium acetate buffer (pH 5.2), and the mixture was stirred for dissolution. The mixture was heated at 80° C. and polyinosinic acids having an arbitrary phosphate rearrangement rate were sampled while monitoring the phosphate rearrangement rate by the method described in Experiment 6. Polyinosinic acid of each phosphate rearrangement rate was heated at 60° C. in a borate buffer (pH 8.5) to shorten the chain length until the average chain length became 200±50 b while monitoring the chain length according to the method described in Experiment 5. The results are shown in Table 3. The respective chain-shortened polyinosinic acid solutions so obtained were dialyzed and lyophilized in a conventional manner to obtain a lyophilized product.

TABLE 3

| Rearrangement reaction | | Chain-shortening reaction | | | |
|---|---|---|---|---|---|
| Temp. | Time (hour) | Temp. | Time (hour) | Average chain length | Phosphate rearrangement rate |
| 80° C. | 2.5 | 60° C. | 3 | 227 b | 0.7% |
|  | 6.5 |  | 1.5 | 230 b | 2.0% |
|  | 9 |  | 4 | 191 b | 2.8% |
|  | 16.5 |  | 2 | 228 b | 4.2% |

EXAMPLE 14

To about 200 mg of sodium polycytidylate ($S°_{20,w}$ (sedimentation constant): 8.6, Yamasa Corporation) was added 0.2 M acetic acid-sodium acetate buffer (pH 5.2), and the mixture was stirred for dissolution, The mixture was heated at 80° C. and polycytidylic acids having an arbitrary phosphate rearrangement rate were sampled while monitoring the phosphate rearrangement rate by the method described in Experiment 6. Polycytidylic acid of each phosphate rearrangement rate was heated at 70° C. in a borate buffer (pH 8.5) to shorten the chain length until the average chain length became 200±50 b while monitoring the chain length according to the method described in Experiment 5. The results are shown in Table 4. The respective chain-shortened polyinosinic acid solutions so obtained were dialyzed and lyophilized in a conventional manner to obtain a lyophilized product.

TABLE 4

| Rearrangement reaction | | Chain-shortening reaction | | | |
|---|---|---|---|---|---|
| Temp. | Time (hour) | Temp. | Time (hour) | Average chain length | Phosphate rearrangement rate |
| 80° C. | 3 | 70° C. | 3 | 157 b | 1.2% |
|  | 4.5 |  | 1 | 218 b | 1.9% |
|  | 6 |  | 1 | 236 b | 2.7% |
|  | 10 | not-adjusted |  | 170 b | 3.8% |

EXAMPLE 15

Double Stranded Chain-shortened Polynucleotide

Double stranded chain-shortened polynucleotides (double stranded RNAs) were prepared from the following combinations: polyinosinic acid (phosphate rearrangement rate: 0.7%) and polycytidylic acid (phosphate rearrangement rate: 1.2%); polyinosinic acid (phosphate rearrangement rate: 2.0%) and polycytidylic acid (phosphate rearrangement rate:

1.9%); polyinosinic acid (phosphate rearrangement rate: 2.8%) and polycytidylic acid (phosphate rearrangement rate: 2.7%), which have been obtained according to the method of Example 1, 2, 11 or 12. Each double stranded chain-shortened polynucleotides was prepared by dissolving sodium polyinosinate and sodium polycytidylate into Tris-HCl buffer (pH 7, containing 0.15 M NaCl), heating the solution at 80° C. for 5 minutes, and gradually cooling the solution.

COMPARATIVE EXAMPLE 1

This comparative example corresponds to Example 1 above, wherein the preparation is conducted by a conventional method (preparation-1).

To 5 mg of sodium polyinosinate ($S°_{20,w}$ (sedimentation constant): 8.8, Yamasa Corporation) was added 10 mL of injectable water, and the mixture was stirred for dissolution. To the solution was added 10 mL of formamide, and the mixture was heated at 80° C. for 5 hours (phosphate rearrangement rate: 8.9%, average chain length: 628b).

COMPARATIVE EXAMPLE 2

This comparative example corresponds to Example 2 above, wherein the preparation is conducted by a conventional method (preparation-1).

To 5 mg of sodium polycytidylate ($S°_{20,w}$ (sedimentation constant): 8.6, Yamasa Corporation) was added 10 mL of injectable water, and the mixture was stirred for dissolution. To the solution was added 10 mL of formamide, and the mixture was heated at 80° C. for 5 hours (phosphate rearrangement rate: 4.2%, average chain length: 751b).

COMPARATIVE EXAMPLE 3

This comparative example corresponds to Example 1 above, wherein the preparation is conducted by a conventional method (preparation-2).

To 5 mg of sodium polyinosinate ($S°_{20,w}$ (sedimentation constant): 8.8, Yamasa Corporation) was added 10 mL of injectable water, and the mixture was stirred for dissolution. The solution was heated at 90° C. for 8 hours (phosphate rearrangement rate: 7.1%, average chain length: 213 b).

COMPARATIVE EXAMPLE 4

This comparative example corresponds to Example 2 above, wherein the preparation is conducted by a conventional method (preparation-2).

To 5 mg of sodium polycytidylate ($S°_{20,w}$ (sedimentation constant): 8.6, Yamasa Corporation) was added 10 mL of injectable water, and the mixture was stirred for dissolution. This solution was heated at 90° C. for 12 hours (phosphate rearrangement rate: 4.2%, average chain length: 289 b).

COMPARATIVE EXAMPLE 5

A double stranded chain-shortened polynucleotide (double stranded RNA) was prepared by combining polyinosinic acid (phosphate rearrangement rate: 4.2%) with polycytidylic acid (phosphate rearrangement rate: 3.8%), which have been prepared in Examples 11 and 12, respectively. The said double stranded chain-shortened polynucleotides was prepared by dissolving sodium polyinosinate and sodium polycytidylate into Tris-HCl buffer (pH 7, containing 0.15 M NaCl), heating the solution at 80° C. for 5 minutes, and gradually cooling the solution.

Experiment 1 Influence of Average Chain Length on Pharmacological Activity

The pharmacological activity of the composition of Example 9 was evaluated in vitro according to the growth inhibitory action on HeLa S3 cancer cells. HeLa S3 cancer cells were inoculated in 96-well plate at a density of $10^4$ cell/well and cultured for 24 hours or longer, when the sufficient adhesion of the cell to the plate was confirmed. To the plate was added a composition of the present invention, and the cultivation was continued. After 3-day-cultivation in a $CO_2$ incubator, the number of viable cells was counted by an MTT method. The cell growth inhibition rate was calculated according to the following formula (I). The results are shown in Table 5.

$$\text{Cell growth inhibition rate (\%)} = \frac{\text{Absorbance of complex} - \text{treated group}}{\text{Absorbance of control group}} \times 100 \quad (I)$$

TABLE 5

| Average chain length (Phosphate rearrangement rate) | | Cell growth inhibition rate against cancer cell HeLa S3 (%) Concentration of poly(I), Na + poly(C), Na | | | | |
|---|---|---|---|---|---|---|
| Poly(I)* | Poly(C)** | 0.1 | 1 | 10 | 100 | 1000 |
| >>1000 b[a] | >>1000 b[b] | 86 | 100 | 100 | 100 | 100 |
| 1419 b (0.1%) | 1923 b (0.1%) | 79 | 98 | 100 | 100 | 100 |
| 982 b (0.1%) | 907 b (0.2%) | 65 | 96 | 100 | 100 | 100 |
| 524 b (0.4%) | 489 b (0.3%) | 23 | 85 | 98 | 100 | 100 |
| 360 b (0.2%) | 318 b (0.1%) | 17 | 70 | 97 | 100 | 100 |
| 118 b (1.2%) | 139 b (0.8%) | 9 | 45 | 89 | 98 | 100 |
| 84 b (1.8%) | 76 b (1.2%) | 0 | 0 | 6 | 72 | 92 |
| 32 b (6.8%) | 27 b (4.2%) | 0 | 0 | 0 | 18 | 48 |

*poly(I) = polyinosinic acid poly(I), Na = polyinosinate, sodium salt
**poly(C) = polycytidylic acid poly(C), Na = polycytidylate, sodium salt
[a]polyinosinate, sodium salt (Yamasa Corporation)
[b]polycytidylate, sodium salt (Yamasa Corporation)

It is apparent from Table 5 that the cell growth inhibiting action of each composition on HeLa S3, a cancer cell strain, is highly correlated with the average chain length. Table 5 reveals that polyinosinic-polycytidylic acids having long chain length of more than 1,000 b, which are generally used as interferon inducing agents, show the strongest growth inhibiting action. The chain-shortened polyinosinic-polycytidylic acids of the present invention having an average chain length ranging from 0.1 kb to 1 kb and containing less phosphate groups rearranged still have sufficiently high growth inhibiting activity, although it is slightly lower. Such a growth inhibitory action decreased steeply in a polynucleotide having the average chain length of under 100 b, and those having the average chain length similar to that of oligonucleotides show little action.

Experiment 2 Influence on Marrow Cells

The toxicity evaluation was carried out on the basis of the toxicity on bone marrow. Male ddY mice (male, 8 week old) were administered by intravenous injection each of the following samples: commercially available sodium polyinosinate ($S°_{20,w}$ (sedimentation constant): 8.8, Yamasa Corporation) and sodium polycytidylate ($S°_{20,w}$ (sedimentation constant): 8.6, Yamasa Corporation), and polyinosinic acid and polycytidylic acid containing less phosphate groups rearranged, which have the average chain length of 982 b and 907 b, respectively, and are prepared in Examples 5 and 6. On the next day, bone marrow cells were collected from thigh bone, stained with New methylene blue and Giemsa, and observed to count the numbers of reticulocytes and matured erythrocytes. The results are shown in Table 6, wherein the bone marrow toxicity is expressed as a ratio of the number of reticulocytes to the total number of matured erythrocytes as defined by the following formula. The mark * means that there is a significant difference based on the multi-comparison method of Dunnett at significant level of p<0.01 between the test group and control group received intravenous administration of a vehicle without polynucleotide.

Bone marrow toxicity =

$$\frac{\text{Number of reticulocyte}}{\text{Number of reticulocyte + Number of matured erythrocyte}}$$

TABLE 6

| Average chain length | | | Bone marrow | Difference from |
|---|---|---|---|---|
| Poly(I)[1] | Poly(C)[2] | Dose | toxicity | Control |
| >>1000 b[a] | >>1000 b[b] | 1 mg/kg | 0.23* | 39% |
|  |  | 5 mg/kg | 0.15* | 61% |
| 982 b | 907 b | 5 mg/kg | 0.31 | 17% |
|  |  | 25 mg/kg | 0.29 | 24% |

[1] poly(I) = polyinosinic acid
[2] poly(C) = polycytidylic acid
[a] polyinosinate, sodium salt (Yamasa Corporation)
[b] polycytidylate, sodium salt (Yamasa Corporation)

It is apparent from Table 6 that the change in bone marrow toxicity based on that of control reached as high as 39% at the dosage of 1 mg/kg in the cases of polyinosinic-polycytidylic acid which has a long chain length of over 1,000 b and are generally used as an interferon inducing agent, while there is no significant difference compared to control in the cases of the chain-shortened polyinosinic-polycytidylic acid which has an average chain length between 0.1 kb and 1 kb and contains less phosphate groups rearranged even at 25-fold dosage. The results above revealed that the toxicity of polyinosinic acid and polycytidylic acid is highly correlated with the average chain length, similar to pharmacological activity thereof. It was unexpectedly surprising finding that the chain-shortened polynucleotide of the present invention could improve such a toxicity significantly.

Experiment 3 Cell Growth Inhibitory Action (In Vitro) on A431 Cancer Cell (Average Chain Length: 200±50 b)

A composition was prepared in a manner similar to that described in Example 9 using the polyinosinic acid (phosphate rearrangement rate: 0.7-4.2%) and polycytidylic acid (phosphate rearrangement rate: 1.2-3.8%) obtained in Examples 11 and 12, and the chain-shortened polyinosinic acid and polycytidylic acid obtained in Examples 1 and 2. A431 cancer cells were inoculated in a 96-well plate at a density of $10^4$ cell/well and cultured for 5 hours or longer, when the sufficient adhesion of the cell to the plate was confirmed. To the plate was added each of the composition and cultivation was continued. After 3-day-cultivation in a $CO_2$ incubator, the number of viable cells was counted by an MTT method. The cell growth inhibition rate was calculated according to the formula (I), and the total concentration of sodium polyinosinate and sodium polycytidylate corresponding to 50% cell growth inhibition rate ($IC_{50}$) was calculated. The results are shown in Table 7.

TABLE 7

|  |  | Phosphate rearrangement rate of polyinosinic acid | | | | |
|---|---|---|---|---|---|---|
|  |  | 0.2% | 0.7% | 2.0% | 2.8% | 4.2% |
| Phosphate | 0.1% | 1.2 | 1.2 | 1.3 | 3.5 | 6.5 |
| rearrangement | 1.2% | 1.1 | 1.2 | 1.4 | 5.6 | 10 |
| rate of | 1.9% | 1.2 | 1.3 | 1.4 | 8.2 | 17 |
| polycytidylic | 2.7% | 4.2 | 6.2 | 10 | 17 | 36 |
| acid | 3.8% | 7.8 | 11 | 23 | 41 | 66 |

50% cell growth inhibition concentration (ng/ml) against A431 cancer cells

As apparent from Table 7, the cell growth inhibiting action of the composition on A431 cancer cell was highly correlated with the phosphate rearrangement rate. That is, as the increase of phosphate groups rearranged from 3' position to 2' position, the growth inhibiting action tends to become weaker, irrespective of polyinosinic acid or polycytidylic acid. It is notable that the growth inhibiting action was remarkably strong in a combination of chain-shortened polyinosinic acid with chain-shortened polycytidylic acid each containing less phosphate groups rearranged (phosphate rearrangement rate is 3% or less, particularly 2% or less) of the present invention. On the other hand, in a combination of polyinosinic acid with polycytidylic acid each having a phosphate rearrangement rate of more than 2%, particularly 3% or more, the action tended to become weaker synergically. For example, in Table 7, a combination of polyinosinic acid (phosphate rearrangement rate: 2.0%) with polycytidylic acid (phosphate rearrangement rate: 1.9%) shows the improved $IC_{50}$ rate by 12-fold or 47-fold as compared with combinations of polyinosinic acid (phosphate rearrangement rate: 2.8%) with polycytidylic acid (phosphate rearrangement rate: 2.7%), and polyinosinic acid (phosphate rearrangement rate: 4.2%) with polycytidylic acid (phosphate rearrangement rate: 3.8%), respectively. It was extremely unexpected that the pharmacological activity increases thus steeply as the rearrangement rate of phosphate group from 3' position to 2' position decreases across 3%, particularly 2%, as the boundary.

Experiment 4 Influence of Phosphate Rearrangement on Melting Temperature (Tm) and Pharmacological Activity A double stranded RNA dissociates into two single stranded RNAs as the temperature is elevated to a given degree. The temperature varies depending on the kind of bases composing an RNA and is specific thereto. Accordingly, the said temperature is defined as the melting temperature of a double stranded RNA and is generally referred to as "Tm value". There are various methods for measuring the Tm value. In the present experiment, the Tm value of double stranded RNAs shown in Example 13 and Comparative Example 5 were measured by the most common method, i.e., absorptiometry. The results are shown in Table 8. The $IC_{50}$ values shown in Table 8 are obtained in Experiment 3.

TABLE 8

| Phosphate rearrangement rate of polyinosinic acid (%) | Phosphate rearrangement rate of polycytidylic acid (%) | Melting Temperature (Tm value) (° C.) | $IC_{50}$ (ng/ml) |
|---|---|---|---|
| 0.2 | 0.1 | 61 | 1.2 |
| 0.7 | 1.2 | 62 | 1.2 |
| 2.0 | 1.9 | 59 | 1.4 |
| 2.8 | 2.7 | 59 | 17 |
| 4.2 | 3.8 | 58 | 66 |

As a result of measurement of the Tm value in polyinosinic—polycytidylic acid having phosphate rearrangement rate range of about 0 to 4%, no remarkable difference was found in each combination. (For polyinosinic-polycytidylic acid having long chain length generally used as interferon inducing agents, the Tm value is 61° C.). It was revealed that polyinosinic-polycytidylic acid having phosphate rearrangement rate between about 0 and 4% can form double helical structure characteristic of double stranded RNA. However, it was also revealed that the immune activating action and carcinostatic action, which are the main medicinal effects of polyinosinic-polycytidylic acid, are affected not only by the double helical structure of a double stranded RNA but also the rearrangement rate of phosphate group, because the pharmacological activity varies as much as by 4-fold to 50-fold or more when the phosphate rearrangement rate changes across 2%-3% as the boundary, as shown in Experiment 3. In addition, it was unexpectedly surprising finding that the pharmacological activity increases steeply when the rearrangement rate of phosphate group from 3' position to 2' position changes across 2%-3% as the boundary.

Experiment 5 Measurement of Average Chain Length of Chain-shortened Polynucleotide (GPC Method)

The average chain length was measured using an aqueous solution of 1 mg/mL polynucleotide by gel permeation chromatography (GPC) under the following conditions.

| GPC operating conditions: | |
|---|---|
| Detection: | UV at 260 nm |
| Column: | Tosoh TSK gel G5000PWXL 7.8 mmϕ × 300 mm |
| Mobile phase: | 50 mM Tris-HCl buffer (pH 7.5) containing 7 M urea |
| Flow rate: | 0.5 mL/min. |
| Size marker: | RNA Ladder (1770 b, 1520 b, 1280 b, 780 b, 530 b, 400 b, 280 b, 155 b) (Gibco BRL) |

Experiment 6 Measurement of Phosphate Rearrangement Rate

To 1 mL of an aqueous solution of 1 mg/mL polynucleotide was added 3.2 mL of aqueous solution of 500 U/mL nuclease $P_1$ (derived from Penicillium citrinum, Seikagaku Corporation), and diluted with water to make the volume 5 mL. The aqueous solution was allowed to react for 1 hour on a water bath at 37° C. Water was added to the reaction mixture to make the volume 10 mL and 3.2 mL portion was separated therefrom. To the separated solution was added 0.8 mL of an aqueous solution of 0.1 U/mL alkaline phosphatase (derived from Calf intestine, Seikagaku Corporation), and allowed to react on a water bath at 37° C. for 30 minutes. The solution was appropriately diluted, examined by a liquid chromatography under the following conditions to determine a dimer having a 2'-5' phosphodiester bond and the phosphate rearrangement rate.

| Liquid chromatography operating conditions: | |
|---|---|
| Detection: | UV at 260 nm |
| Column: | Shiseido Capcell pack $C_{18}$ UG120 5 μm 4.6 mmϕ × 250 mm |
| Mobile phase: | Mixed solution (95:5) of 50 mM phosphate buffer (pH 8) containing 5 mM tetrabutylammonium hydrogen sulfate and methanol |
| Flow rate: | 1 mL/min. |

The invention claimed is:

1. A method for preparing a chain-shortened polynucleotide or salt thereof in which the proportion of a 2'-5' phosphodiester bond is up to 3% based on the total number of phosphodiester bonds, comprising:
   a. hydrolyzing a polynucleotide or salt thereof in a solution at pH 7 to 10 at a temperature between 20 and 110° C. to shorten the chain length of the polynucleotide or salt thereof; and
   b. monitoring the phosphate rearrangement rate of the shortened polynucleotide or salt thereof to confirm the proportion of 2'-5' phosphodiester bonds is 3% or less based on the total number of phosphodiester bonds.

2. The method according to claim 1, wherein the polynucleotide is polyinosinic acid or analogue thereof, polycytidylic acid or analogue thereof, polyadenylic acid or analogue thereof, or polyuridylic acid or analogue thereof.

3. The method for preparing the chain-shortened polynucleotide or salt thereof according to claim 1, wherein the chain shortened polynucleotide or salt thereof has an average chain length of between 0.1 k bases and about 1 k bases.

* * * * *